United States Patent [19]

Yonezawa

[11] Patent Number: 4,605,791
[45] Date of Patent: Aug. 12, 1986

[54] PROCESS FOR PURIFICATION OF TECHNICAL GRADE PENTACHLOROPHENOL

[75] Inventor: Toyozo Yonezawa, Minami, Japan

[73] Assignee: Yonezawa Chemical Industry Co., Ltd., Kyoto, Japan

[21] Appl. No.: 743,471

[22] Filed: Jun. 7, 1985

[51] Int. Cl.$^4$ .............................................. C07C 37/68
[52] U.S. Cl. .................... 568/755; 568/749; 568/758; 568/762
[58] Field of Search ............... 568/755, 758, 762, 754, 568/749

[56] References Cited

U.S. PATENT DOCUMENTS

| | | | |
|---|---|---|---|
| 2,131,259 | 9/1938 | Stoesser | 568/755 |
| 3,051,761 | 8/1962 | MacBeth | 568/755 |
| 3,909,365 | 9/1975 | Christena | 568/755 |
| 4,058,457 | 11/1977 | Manes | 568/755 |
| 4,142,943 | 3/1979 | Kobel | 568/755 |
| 4,228,309 | 10/1980 | Hatcher | 568/755 |

FOREIGN PATENT DOCUMENTS 2810142  9/1979  Fed. Rep. of Germany ...... 568/755

Primary Examiner—Werren B. Lone
Attorney, Agent, or Firm—Wenderoth, Lind & Ponack

[57] ABSTRACT

Process for purification of technical grade pentachlorophenol by immersing the pentachlorophenol in an aqueous alkaline solution or suspension, separating an insoluble portion from the resultant mixture, dissolving the insoluble portion in an aqueous alkaline solution, treating the solution with active charcoal, removing the active charcoal, adding copper sulfate to the solution, removing the deposit which forms from the solution, and recovering pentachlorophenol from the solution. Alternatively, the steps of treatment with active charcoal and addition of copper sulfate can be reversed.

24 Claims, No Drawings

PROCESS FOR PURIFICATION OF TECHNICAL GRADE PENTACHLOROPHENOL

BACKGROUND OF THE INVENTION

This invention relates to a process for purification of technical grade pentachlorophenol in order to obtain high-purity pentachlorophenol which is adapted for use as an active ingredient in agricultural chemicals or industrial antiseptics that are free from pollution problems.

Pentachlorophenol is industrially manufactured by the chlorination of phenol, but the technical grade of pentachlorophenol obtained in this way contains as impurities various phenolic acid substances and non-phenolic neutral substances.

Among these impurities are chlorodibenzodioxines or chlorodibenzofurans that are known to be strongly toxic, and substances that are said to be the precursors of these compounds, such as for example, chlorodiphenyl ethers, chlorophenoxyphenols, and chlorodihydroxybiphenyls, so that in the application of technical grade pentachlorophenol to agricultural chemicals or industrial antiseptics that are free from pollution problems it was eagerly desired to remove the above described harmful impurities, but at present no effective method for the removal of these impurities has yet been established.

SUMMARY OF THE INVENTION

In view of the above described situation the present inventors investigated the process for removing the above described undesirable impurities contaminated in technical grade pentachlorophenol, and as the result is was noticed that pentachlorophenol differs from any of the impurities in its solubility in alkaline aqueous solutions. This led further to the discovery that by taking advantage of this difference in solubilities in combination with adsorption treatment with active charcoal, the above described impurities contaminated in technical grade pentachlorophenol can be effectively separated and removed, and thus this invention could be achieved.

That is to say, the object of this invention is to provide a process for purification of pentachlorophenol in order to obtain highpurity pentachlorophenol which is adapted for use as agricultural chemicals or industrial antisepics that are free from pollution problems by effectively removing the undesirable impurities contaminated in technical grade pentachlorophenol from said pentachlorophenol.

The other objects of this invention will become apparent from the following description.

DETAILED DESCRIPTION OF THE INVENTION

The characteristic feature of this invention resides in (1) that the process for purification of technical grade pentachlorophenol comprises a step of immersing said pentachlorophenol in an aqueous solution or suspension of one member selected from the group consisting of sodium bicarbonate, potassium bicarbonate, ammonium carbonate, ammonia, and calcium carbonate and dissolving the insoluble portion which is obtained by the removal of the solution containing the dissolved out material, in an aqueous solution of sodium carbonate or potassium carbonate or in a hot aqueous solution of an alkaline substance which is capable of dissolving pentachlorophenol at elevated temperatures, whereby the material still remaining undissolved is removed, a step of carrying out first an adsorption treatment with active charcoal by contacting the resulting solution with active charcoal and after the separation and removal of both the adsorbed material and active charcoal adding a small quantity of copper sulfate to the thus obtained solution and then separating and removing the deposit which forms, or alternatively, the steps of carrying out said active charcoal treatment and copper sulfate treatment are conducted in the reverse order, and the step of recovering a pentachlorophenol from the finally obtained solution, and (2) that the process for purification of technical grade pentachlorophenol comprises a step of dissolving said pentachlorophenol in an aqueous solution containing a slight excess of sodium carbonate or potassium carbonate or a hot aqueous solution of an alkaline substance which is capable of dissolving pentachlorophenol at elevated temperatures and then removing the insoluble matter, a step of carrying out an adsorption treatment by contacting the resulting solution with active charcoal and after the separation and removal of both the adsorbed material and active charcoal adding a small quantity of copper sulfate to the thus obtained solution and then separating and removing the deposit which forms, or alternatively, the steps of carrying out said active charcoal treatment and copper sulfate treatment are conducted in the reverse order, and a step of recovering pentachlorophenol. In embodiment (2), where use is made of the above described aqueous solution of sodium carbonate or potassium carbonate, the deposit of pentachlorophenol which is formed when the solution then obtained is acidified, is immersed in an aqueous solution or suspension of one member selected from the group consisting of sodium bicarbonate, potassium bicarbonate, ammonium carbonate, ammonia, and calcium carbonate, and the dissolved out material is removed.

This invention is based on the information such that on the one hand, although pure pentachlorophenol does not dissolve in an aqueous solution of sodium bicarbonate, potassium bicarbonate, ammonia, ammonium carbonate, etc. at room temperature, technical grade pentachlorophenol contains a few per cent of some substances which dissolve in the above described aqueous solutions at room temperature. On the other hand, although pure pentachlorophenol dissolves in an aqueous solution of caustic soda, caustic potash, sodium carbonate, or potassium carbonate at room temperature and in an aqueous solution of sodium sulfite or potassium sulfite at elevated temperatures, respectively, technical grade pentachlorophenol contains a few per cent of some substances which do not dissolve in the above described aqueous solutions, and further the above described substances contained in an amount of a few per cent in technical grade pentachlorophenol are anything but pentachlorophenol in view of their melting point, molecular weight, and sublimation property.

Therefore, in this invention, at first technical grade pentachlorophenol is immersed in an aqueous solution or suspension of sodium bicarbonate, potassium bicarbonate, ammonium carbonate, ammonia, or calcium carbonate so as to dissolve and remove the impurities contained in said pentachlorophenol as soluble matter, and the pentachlorophenol in the thus obtained insoluble portion is dissolved in an aqueous solution of sodium carbonate or potassium carbonate or a hot aqueous solution of an alkaline substance which is capable of dissolving pentachlorophenol at elevated temperatures such as sodium sulfite, potassium sulfite, etc., whereby the insoluble matter consisting of undissolved impurities is removed (the above described invention numbered (1)). Alternatively, technical grade pentachlorophenol is dissolved in an aqueous solution of sodium carbonate or potassium carbonate or a hot aqueous solution of the above described alkaline substance whereby the insolubles consisting of the impurities remaining undissolved are removed (the above described invention numbered (2)).

In this connection, when technical grade pentachlorophenol is immersed in an aqueous solution of sodium bicarbonate as well as potassium bicarbonate about 5% by weight of it is dissolved, and when immersed in an aqueous solution of ammonia as well as ammonium carbonate about 2% by weight is dissolved, but in view of the fact that the substance obtained as a deposit by acidifying the resulting solution shows a melting point of 176° C. and a molecular weight of 530 it is regarded as an impurity quite different from pentachlorophenol.

Further, as the above described hot aqueous soultion of an alkaline substance which is capable of dissolving pentachlorophenol, hot aqueous solutions of $K_2SO_3$, $NA_2SO_3$, $NaHSO_3$, $NaNO_2$, $Na_2S_2O_3$, $KNO_2$, $K_2S_2O_3$, $(NH_4)_2SO_3$, $NH_4NS_3$, etc. may be exemplified. Among them the preferable ones are hot aqueous solutions of sodium sulfite and potassium sulfite from the standpoint of solubility difference against the impurities.

In accordance with the process of this invention, taking advantage of the solubility difference between pentachlorophenol and impurities contained in technical grade pentachlorophenol in said alkaline substance, most of the impurities contained in technical grade pentachlorophenol are removed as above described, and by subjecting the resulting product to adsorption treatment with active charcoal the impurities still remaining in the pentachlorophenol are more completely removed by being adsorbed with charcoal.

That is to say, the above described adsorption treatment with active charcoal is based on the information that the adsorbability to active charcoal of the impurities contained in technical grade pentachlorophenol is higher than that of pentachlorophenol.

Next, in the above described invention (1) there can be recovered a pure product of pentachlorophenol which contains substantially no impurities consisting of non-phenolic neutral substances, and phenolic acid substances in such a way that to the solution containing the pentachlorophenol, from which the impurities have been removed by the adsorption treatment with active charcoal as above described, is slowing added a small quantity of copper sulfate with stirring, whereby trace amounts of impurities still remaining the allowed to deposit as copper salt which is removed. In addition, the order of the above described active charcoal treatment and copper sulfate treatment may be reversed.

Also, in the above described invention (2), after the impurities have been removed by the adsorption treatment with active charcoal as above described, to the resulting solution containing pentachlorophenol is slowly added a small quantity of copper sulfate with stirring to remove the remaining inpurities as copper salt by deposition, and then, by acidifying the solution thus obtained a deposit consisting chiefly of pentachlorophenol is allowed to be formed. In addition, the order of said active charcoal treatment and copper sulfate treatment may be reversed. Subsequently, in case where use was made of an aqueous solution of sodium carbonate or potassium carbonate, said deposit is immersed in an aqueous solution or suspension of sodium bicarbonate, potassium bicarbonate, ammonium carbonate, ammonia, or calcium carbonate taking advantage of the solubility difference in aqueous solutions of these alkaline substances between pentachlorophenol and impurities, whereby trace amounts of impurities remaining in said deposit are removed by dissolution, so that there can be recovered a pure product of pentachlorophenol which contains substantially no impurities consisting of non-phenolic neutral substances and phenolic acid substances. In addition, where use was made of a hot aqueous solution of an alkaline substance which is capable of dissolving technical grade pentachlorophenol at elevated temperatures such as, for example, a hot aqueous solution of sodium sulfite or potassium sulfite, when the solution of the technical grade pentachlorophenol obtained by dissolving it in said hot aqueous solution is cooled even to about 20° C., the dissolved impurities remain as such in the solution, and as these soluble impurities correspond to the impurities soluble in aqueous solutions of sodium bicarbonate, potassium bicarbonate, etc., the step of immersing the above described deposit in these aqueous solutions need not be carried out.

In this invention, when technical grade pentachlorophenol or the insoluble portion which remains after technical pentachlorophenol has been immersed in an aqueous solution (or suspension) of the above described alkaline substance such as sodium bicarbonate, potassium bicarbonate, etc. and then the impurities dissolved out have been removed, is dissolved in an aqueous solution of sodium carbonate or potassium carbonate, it is possible to carry out the dissolution even at room temperature. However, as the sodium carbonate or the potassium carbonate reacts with carbon dioxide gas to form sodium bicarbonate or potassium bicarbonate (in which pentachlorophenol is insoluble), an excess (more than 100% over the theoretical amount) of sodium carbonate or potassium carbonate is required for the dissolution, and therefore, in practice, it is preferable to carry out the dissolution at an elevated temperature of 70°–95° C., or more preferably 80°–90° C. (for example, sodium bicarbonate changes into sodium carbonate at a temperature above 65° C.). In case where the dissolution is carried out at such an elevated temperature hot filtration can be used to advantage for the removal of the insolubles.

Also, when use is made of hot aqueous solutions of sodium sulfite, potassium sulfite, and other above described alkaline substances for the dissolution, it is desirable that technical grade pentachlorophenol or the same from which the soluble portion has been removed by immersing it in an aqueous solution (or suspension) of sodium bicarbonate, potassium bicarbonate, ammonium carbonate, ammonia, or calcium carbonate, is added to water and while heating to 90°–100° C. the pentachlorophenol is dissolved by adding thereto an alkaline substance such as sodium sulfite, potassium sulfite, etc. slowly in portions.

Furthermore, when the aqueous solution obtained by dissolving the pentachlorophenol portion in an aqueous solution of sodium carbonate has been allowed to deposit pentachlorophenol by the introduction, preferably under pressure, of carbon dioxide gas and then the mother liquor is heated to a temperature above 65° C., an aqueous solution of sodium carbonate can be reproduced, so that the solution can be used repeatedly for the dissolution of pentachlorophenol. Also, when the solution obtained by dissolving the pentachlorophenol portion in a hot aqueous solution of sodium sulfite is allowed to deposit pentachlorophenol by cooling, said sodium sulfite remains in the mother liquor, so that said mother liquor can be used repeatedly for the dissolution of pentachlorophenol.

Subsequently, in this invention the aqueous solution containing chiefly pentachlorophenol which was obtained from technical grade pentachlorophenol in the above described way is subjected to adsorption treatment by contacting with active charcoal, and in the case of the aqueous solution resulting from dissolving in an aqueous solution of sodium carbonate the adsorption treatment may be achieved even after cooling the solution, but in the case of the aqueous solution resulting from dissolving in an aqueous solution of sodium sulfite it should preferably be carried out while hot. As for the active charcoal it is better to use it in an amount of about 3% by weight on the basis of pentachlorophenol, and the adsorption treatment is carried out either by adding active charcoal to the above described aqueous solution with stirring or by passing said aqueous solution through a layer of active charcoal.

The amount of the substances adsorbed by this adsorption treatment is in the order of about 2% on the basis of the pentachlorophenol in the above described aqueous solution, and what is obtained by extracting from the adsorbed substances with benzene shows a melting point of 120° C. and a molecular weight of 528, so that it is regarded as an impurity other than pentachlorophenol.

After both the active charcoal and the adsorbed material have been removed from the aqueous solution which was subjected to the adsorbtion treatment with active charcoal, to the resulting solution is added an aqueous solution containing copper sulfate in an amount sufficient to make 1-2% of the pentachlorophenol present in the solution change into the copper salt, and thus the impurities still remaining in the aqueous solution are allowed to deposit as copper salt which is removed. In this connection, on account of the fact that the substance obtained by the decomposition of this deposited copper salt shows a melting point of 70° C. and a molecular weight of 530 it is regarded as an impurity other than pentachlorophenol.

In the above described invention (1), the solution obtained in the above described way contains substantially impurity-free pentachlorophenol, and therefore, hydrochloric acid is added thereto to deposit pure pentachlorophenol which is recovered.

Further, in the above described invention (2) hydrochloric acid is added to the aqueous solution, from which the above described copper salt has been removed, to deposit pentachlorophenol. In case where use was made of the above described aqueous solution of sodium carbonate or potassium carbonate, subsequently this deposit is further immersed in an aqueous solution or suspension of sodium bicarbonate, potassium bicarbonate, ammonium carbonate, ammonia, or calcium carbonate so as to remove trace amounts of impurities contaminated in said deposit by dissolution, and thus substantially impurity-free pentachlorophenol is recovered.

As above described, this invention makes it possible to recover pure pentachlorophenol substantially free from the above described inpurities from technical grade pentachlorophenol by treating said technical grade pentachlorophenol with aqueous solutions of various alkaline substances and subjecting its aqueous solution to adsorption treatment with active charcoal, taking advantage of the solubility difference against various alkaline substances between pentachlorophenol in said technical pentachlorophenol and impurities contaminated therein consisting of various phenolic acid substances and non-phenolic neutral substances as well as the adsorbability difference against active charcoal. Therefore, this invention is very useful when pentachlorophenol is utilized in agricultural chemicals or the like, and in industrial antiseptics or the like, to render them free from pollution problems.

With reference to some examples this invention and its effects will be more concretely explained below.

EXAMPLE 1

200 g of technical grade pentachlorophenol ground to 325 mesh was immersed in 1500 cc of 5% aqueous solution of sodium bicarbonate and stirred for 3 hours at room temperature, whereby a small quantity of carbon dioxide gas was generated. After the immersion the insoluble matter was filtered off and collected. This insoluble matter was placed in a solution prepared by dissolving 40 g of sodium carbonate in 1500 cc of water and heated to 80°–90° C. (whereby carbon dioxide gas was generated) so as to dissolve the pentachlorophenol present in said insoluble matter, and the still remaining insoluble matter was removed by filtration.

Next, to the solution thus obtained was added 6 g of active charcoal, and after 30 min. of stirring at 80° C. the active charcoal was removed by filtration. To the resulting solution was slowly added 0.9 g of copper sulfate with stirring, and after 1 hr. of stirring the copper salt deposited was removed by filtration.

By adding hydrochloric acid to the solution obtained in the above described way pentachlorophenol was allowed to deposit and recovered.

The yield was 166 g, and the pentachlorophenol thus obtained contained substantially no impurities such as non-phenolic neutral substances, chlorophenoxyphenols, and chlorodihydroxybiphenyls.

EXAMPLE 2

This example is one embodiment of this invention wherein it is shown that sodium bicarbonate may be reproduced from the mother liquor which is recovered after the separation of the pure pentachlorophenol therefrom by deposition, provided that carbon dioxide gas absorption is used instead of acidification employed in Example 1.

By introducing carbon dioxide gas into the solution of purified sodium salt of pentachlorophenol obtained in Example 1 under 1 atm. at room temperature, under 1 atm. at 0° C., and under 5 atm. at room temperature, respectively, so as to effect adsorption, there was obtained 166 g of pentachlorophenol deposited in each case. After the deposit has been separated and recovered, the remaining mother liquor (solution of sodium bicarbonate) was heated to 80°–90° C. to give an aqueous solution of sodium carbonate, which was used repeatedly for the dissolution of pentachlorophenol.

EXAMPLE 3

200 g of technical grade pentachlorophenol was placed in a solution prepared by dissolving 45 g (a slight excess) of sodium carbonate in 1500 cc of water and heated to 70°–90° C. with stirring to effect dissolution.

When the carbon dioxide gas cease to evolve the insoluble matter was filtered off, and 6 g of active charcoal was added to the resulting solution. After 1 hr. of stirring the active charcoal was filtered off. Then, to the resulting solution was added an aqueous solution containing 0.9 g of dissolved copper sulfate and after several hr. of stirring the copper salt deposited was removed by filtration.

Next, the solution obtained in the above described way was acidified with the addition of hydrochloric acid to deposit pentachlorophenol, and to the deposit were added 7 g of sodium bicarbonate and 1000 cc of water. After 3 hr. of stirring the liquid portion was removed to give 168 g of pure pentachlorophenol. This purified pentachlorophenol was substantially free from the above described impurities.

EXAMPLE 4

This example illustrates the case where the dissolution of pentachlorophenol is carried out in a hot aqueous solution of sodium sulfite.

At first the quantity of sodium sulfite required for the pentachlorophenol to completely dissolve was found as follows. 26.6 g of pure pentachlorophenol was placed in 500 cc of water, and while heating to 90°–100° C., sodium sulfite was slowly added thereto in portions, whereby the quantity of sodium sulfite required for the pentachlorophenol to completely dissolve was found to be 27 g. In addition, when the resulting solution was left to cool and the pentachlorophenol deposited at 20° C. was recovered there was obtained 25.5 g (yield 96%).

To 26.6 g of technical grade pentachlorophenol were added 27 g, which was found in the above described way, of sodium sulfite and 250 cc of water, and the mixture was heated to 90°–100° C. for 2 hours. To the resulting solution, from which the insoluble matter was filtered off while hot, was added 0.8 g of active charcoal, and the mixture was heated to 90°–100° C. for 30 minutes, after which the active charcoal was removed by hot filtration.

To the resulting solution was added an aqueous solution containing 0.1 g of copper sulfate at 90°–100° C., and after the above described temperature was maintained for one hour, the copper salt deposited was removed by hot filtration. Then, the resulting solution was cooled to 20° C. and the pentachlorophenol deposited was recovered. The yield was 21.9 g (or 82.3%) and the above described insoluble matter was 2.3 g (8.5%).

EXAMPLE 5

In accordance with the same procedure as described in Example 4 the quantity of potassium sulfite required for 26.6 g of pentachlorophenol to completely dissolve was found to be 32 g.

Thus, to 26.6 g of technical grade pentachlorophenol were added 32 g of potassium sulfite and 500 cc of water, and the purification treatment was carried out in the same manner as described in Example 4, which gave 20.1 g of pure pentachlorophenol (yield 75.5%).

EXAMPLE 6

This example is one embodiment of this invention wherein it is shown that the mother liquor (solution of sodium sulfite) which is obtained by dissolving technical grade of pentachlorophenol in a hot aqueous solution of sodium sulfite, treating the resulting solution, from which the insoluble matter was removed, with active charcoal, and after filtering off the active charcoal cooling the filtrate so as to deposit pentachlorophenol, was used three times repeatedly for the dissolution of technical grade pentachlorophenol.

The result is shown in the following table.

TABLE

|  | First time | Second time | Third time |
| --- | --- | --- | --- |
| Yield of pentachlorophenol (%) | 80.1 | 86.9 | 89.2 |
| Proportion of insoluble matter (%) | 8.1 | 7.2 | 6.1 |
| Content of organic matter in mother liquor (%) | 11.8 | 5.9 | 4.7 |

EXAMPLE 7

To 26.6 g (0.1 mole) of technical grade pentachlorophenol were added each 0.22 mole of $NaHSO_3$, $NaNO_2$, $Na_2S_2O_3$, $KHSO_3$, $KNO_2$, $K_2S_2O_3$, and $NH_4HSO_3$, and 500 cc of water, and the purification treatment was carried out in the same manner as described in Example 4.

The yield of the pentachlorophenol obtained was 0.6–1.8 g (or 2.3–6.7%).

That is to say, when using hot aqueous solutions of these alkaline substances the yield of pentachlorophenol is low as compared with use of hot aqueous solution of sodium sulfite or potassium sulfite, but the purification of technical grade pentachlorophenol is still possible.

I claim:

1. A process for purification of technical grade pentachlorophenol which comprises:

immersing said technical grade pentachlorophenol in an aqueous mixture selected from the group consisting of an aqueous solution and an aqueous suspension of a member selected from the group consisting of sodium bicarbonate, potassium bicarbonate, ammonium carbonate, ammonia, and calcium carbonate;

separating an insoluble portion from dissolved material in the resultant mixture;

dissolving said insoluble portion in a member selected from the group consisting of an aqueous solution of sodium carbonate, an aqueous solution of potassium carbonate, and a hot aqueous solution of an alkaline substance which is capable of dissolving pentachlorophenol at 90°–100° C.;

contacting the resulting solution with active charcoal;

separating said active charcoal with adsorbed material thereon from said resulting solution;

adding copper sulfate to the thus obtained solution;

separating and removing the resultant deposit from said solution; and recovering pentachlorophenol from the finally obtained solution.

2. The process as defined in claim 1, wherein said insoluble substance is dissolved in said aqueous solution of sodium carbonate or potassium carbonate at a temperature of 70°–95° C.

3. The process as defined in claim 1, wherein said alkaline substance which is capable of dissolving pentachlorophenol at 90°–100° C. is selected from the group consisting of sodium sulfite and potassium sulfite.

4. The process as defined in claim 11, wherein the treatment with active charcoal is carried out by stirring said solution with addition of said active charcoal.

5. The process as defined in claim 1, wherein the treatment with active charcoal is carried out by allowing said solution to pass through a layer of said active charcoal.

6. The process as defined in claim 1, wherein said copper sulfate is slowly added to said solution with stirring, and said stirring is continued until an equilibirium is reached between material in said solution and said deposit.

7. A process for purification of technical grade pentachlorophenol which comprises:
   immersing said technical grade pentachlorophenol in an aqueous mixture selected from the group consisting of an aqueous solution and an aqueous suspension of a member selected from the group consisting of sodium bicarbonate, potassium bicarbonate, ammonium carbonate, ammonia, and calcium carbonate;
   separating an insoluble portion from dissolved material in the resultant mixture;
   dissolving said insoluble portion in a member selected from the group consisting of an aqueous solution of sodium carbonate, an aqueous solution of potassium carbonate, and a hot aqueous solution of an alkaline substance which is capable of dissolving pentachlorophenol at 90°–100° C.;
   adding copper sulfate to the resulting solution;
   separating and removing the resultant deposit from said solution;
   contacting said solution with active charcoal;
   separating said active charcoal with adsorbed material thereon from said solution; and
   recovering pentachlorophenol from the finally obtained solution.

8. The process as defined in claim 7, wherein said insoluble substance is dissolved in said aqueous solution of sodium carbonate or potassium carbonate at a temperature of 70°–95° C.

9. The process as defined in claim 7, wherein said alkaline substance which is capable of dissolving pentachlorophenol at 90°–100° C. is selected from the group consisting of sodium sulfite and potassium sulfite.

10. The process as defined in claim 7, wherein the treatment with active charcoal is carried out by stirring said solution with addition of said active charcoal.

11. The process as defined in claim 7, wherein the treatment with active charcoal is carried out by allowing said solution to pass through a layer of said active charcoal.

12. The process as defined in claim 7, wherein said copper sulfate is slowly added to said solution with stirring, and said stirring is continued until an equilibirium is reached between material in said solution and said deposit.

13. A process for purification of technical grade pentachlorophenol which comprises:
   dissolving said pentachlorophenol in a member selected from the group consisting of an aqueous solution containing a slight excess of sodium carbonate, an aqueous solution containing a slight excess of potassium carbonate, and a hot aqueous solution of an alkaline substance which is capable of dissolving pentachlorophenol at 90°–100° C.;
   removing insoluble matter from the resultant mixture;
   contacting the resulting solution with active charcoal;
   separating said active charcoal with adsorbed material thereon from said solution;
   adding copper sulfate to the thus obtained solution;
   separating and removing the resultant deposit from said solution; and
   recovering pentachlorophenol from said solution;
   wherein when use is made of said aqueous solution of sodium carbonate or potassium carbonate and said pentachlorophenol is recovered by acidification, said recovered pentachlorophenol is immersed in a member selected from the group consisting of an aqueous solution and an aqueous suspension of a member selected from the group consisting of sodium bicarbonate, potassium bicarbonate, ammonium carbonate, ammonia, and calcium carbonate, and dissolved out material is removed from said pentachlorophenol.

14. The process as defined in claim 13, wherein said technical grade pentachlorophenol is dissolved in said aqueous solution of sodium carbonate or potassium carbonate at 70°–95° C.

15. The process as defined in claim 13, wherein said alkaline substance which is capable of dissolving pentachlorophenol at 90°–100° C. is selected from the group consisting of sodium sulfite and potassium sulfite.

16. The process as defined in claim 13, wherein the treatment with active charcoal is carried out by stirring said solution with addition of said active charcoal.

17. The process as defined in claim 13, wherein the treatment with active charcoal is carried out by allowing said solution to pass through a layer of said active charcoal.

18. The process as defined in claim 13, wherein said copper sulfate is slowly added to said solution with stirring, and said stirring is continued until an equilibrium is reached between material in said solution and said deposit.

19. A process for purification of technical grade pentachlorophenol which comprises:
   dissolving said pentachlorophenol in a member selected from the group consisting of an aqueous solution containing a slight excess of sodium carbonate, an aqueous solution containing a slight excess of potassium carbonate, and a hot aqueous solution of an alkaline substance which is capable of dissolving pentachlorophenol at 90°–100° C.;
   removing insoluble matter from the resultant mixture;
   adding copper sulfate to the resulting solution;
   separating and removing the resultant deposit from said solution;
   contacting said solution with active charcoal;
   separating said active charcoal with adsorbed material thereon from said solution; and
   recovering pentachlorophenol from said solution;
   wherein when use is made of said aqueous solution of sodium carbonate or potassium carbonate and said pentachlorophenol is recovered by acidification, said recovered pentachlorophenol is immersed in a member selected from the group consisting of an aqueous solution and an aqueous suspension of a member selected from the group consisting of sodium bicarbonate, potassium bicarbonate, ammonium carbonate, ammonia, and calcium carbonate, and dissolved out material is removed from said pentachlorophenol.

20. The process as defined in claim 19, wherein said technical grade pentachlorophenol is dissolved in said aqueous solution of sodium carbonate or potassium carbonate at 70°–95° C.

21. The process as defined in claim 19, wherein said alkaline substance which is capable of dissolving pentachlorophenol at 90°–100° C. is selected from the group consisting of sodium sulfite and potassium sulfite.

22. The process as defined in claim 19, wherein the treatment with active charcoal is carried out by stirring said solution with addition of said active charcoal.

23. The process as defined in claim 19, wherein the treatment with active charcoal is carried out by allowing said solution to pass through a layer of said active charcoal.

24. The process as defined in claim 19, wherein said copper sulfate is slowly added to said solution with stirring, and said stirring is continued until an equilibrium is reached between material in said solution and said deposit.

* * * * *